(12) United States Patent
Inada et al.

(10) Patent No.: US 6,420,405 B2
(45) Date of Patent: Jul. 16, 2002

(54) PHARMACEUTICAL COMPOSITION FOR ANGIOTENSIN II-MEDIATED DISEASES

(75) Inventors: Yoshiyuki Inada, Kawanishi (JP); Keiji Kubo, Riverside, CA (US)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/783,579

(22) Filed: Feb. 15, 2001

Related U.S. Application Data

(60) Division of application No. 09/563,855, filed on May 4, 2000, which is a continuation of application No. 09/287,167, filed on Apr. 4, 1999, now abandoned, which is a division of application No. 08/883,040, filed on Jun. 26, 1997, now Pat. No. 5,958,961, which is a division of application No. 08/351,011, filed on Dec. 7, 1994, now Pat. No. 5,721,263, which is a continuation-in-part of application No. 08/254,541, filed on Jun. 6, 1994, now abandoned.

(30) Foreign Application Priority Data

Jun. 7, 1993 (JP) ............................................. 5-133524

(51) Int. Cl.$^7$ ...................... A61K 31/41; A61K 31/405; A61K 31/54
(52) U.S. Cl. ........................ 514/381; 514/364; 514/415; 514/224.8
(58) Field of Search ................................ 514/364, 381, 514/415, 224.8

(56) References Cited

U.S. PATENT DOCUMENTS

| | | | |
|---|---|---|---|
| 4,139,633 A | 2/1979 | Brunner et al. | |
| 4,178,374 A | * 12/1979 | Sweet | 424/246 |
| 4,547,498 A | * 10/1985 | Blume et al. | 514/225 |
| 4,855,289 A | * 8/1989 | Wester et al. | 514/171 |
| 4,880,804 A | 11/1989 | Carini et al. | |
| 4,895,846 A | 1/1990 | Poindexter et al. | |
| 5,128,356 A | 7/1992 | Naka et al. | |
| 5,162,326 A | 11/1992 | Naka et al. | |
| 5,164,509 A | * 11/1992 | Atwal | 548/126 |
| 5,183,899 A | 2/1993 | Naka et al. | |
| 5,187,159 A | * 2/1993 | Greenlee et al. | 514/81 |
| 5,250,554 A | 10/1993 | Naka et al. | |
| 5,284,661 A | 2/1994 | Naka et al. | |
| 5,656,650 A | * 8/1997 | Weinstock | 514/396 |
| 5,736,554 A | * 4/1998 | Spada et al. | 514/303 |
| 6,245,787 B1 | * 6/2001 | Cropp et al. | 514/356 |

FOREIGN PATENT DOCUMENTS

| | | |
|---|---|---|
| DE | 3633114 | 3/1988 |
| EP | 0154009 | 9/1985 |
| EP | 0279750 | 8/1988 |
| EP | 0312157 | 4/1989 |
| EP | 0400835 | 5/1990 |
| EP | 0430300 | 6/1991 |
| EP | 0434038 | 6/1991 |
| EP | 0445811 | 9/1991 |
| EP | 0459136 | 12/1991 |
| EP | 0483683 | 5/1992 |
| EP | 0490587 | 6/1992 |
| EP | 0501892 | 9/1992 |
| EP | 0518033 | 12/1992 |
| EP | 0520423 | 12/1992 |
| EP | 0532410 | 3/1993 |
| EP | 0537937 | 4/1993 |
| FR | 2419728 | 10/1979 |
| GB | 2270841 A | 3/1994 |
| WO | 9100277 | 1/1991 |
| WO | 9100281 | 1/1991 |
| WO | 9210097 | 6/1992 |
| WO | 9317685 | 9/1993 |
| WO | 9409778 | 5/1994 |

OTHER PUBLICATIONS

"Low Doses of Hydrochlorothiazide in Hypertension Antihypertensive and Metabolic Effects", G. Berglund, et al., Europ. J. Clin. Pharmacol., vol. 10, pp. 177–182 (1976).

"Antihypertensive Effect of Various Doses of Hydrochlorothiazide and its Relation to the Plasma Level of the Drug", B. Beerman, et al., Europ. J. Clin. Pharmacol., vol. 13, pp. 195–201 (1978).

"Effects if a nonpeptide angiotensin if receptor antagonist (CV–11974) on [$Ca^{2+}$]; and cell motion in cultured ventricular myocytes", Kinugawa, et al., Europ. J. Pharmacol., vol. 235, pp. 313–316 (1993).

(List continued on next page.)

Primary Examiner—Deborah C. Lambkin
(74) Attorney, Agent, or Firm—Foley & Lardner

(57) ABSTRACT

This invention relates to a pharmaceutical composition for angiotensin II-mediated diseases, which comprises a compound having angiotensin II antagonistic activity of the formula

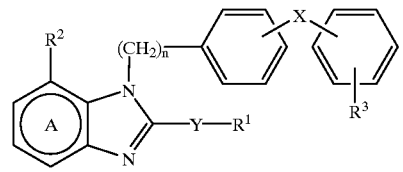

wherein $R^1$ is H or an optionally substituted hydrocarbon residue; $R^2$ is an optionally esterified carboxyl group; $R^3$ is a group capable of forming an anion or a group convertible thereinto; X is a covalent bond between the 2 phenyl rings or a spacer having a chain length of 1 to 2 atoms as the linear moiety between the adjoining phenylene group and phenyl group; n is 1 or 2; the ring A is a benzene ring having 1 or 2 optional substituents in addition to $R^2$; and Y is a bond, —O—, —S(O)m- (wherein m is 0, 1 or 2) or —N($R^4$)— (wherein $R^4$ is H or an optionally substituted alkyl group), or a pharmaceutically acceptable salt thereof in combination with a compound having diuretic activity or a compound having calcium antagonistic activity.

4 Claims, No Drawings

OTHER PUBLICATIONS

"Antihypertensive Effects of Highly Potent and Long–Acting Angiotensin II Subtype–1 Receptor Antagonist, (±)–1–(Cyclohexyloxycarbonyloxy) 2–Ethoxy–1–[[2'–(1H–Tetrazol–5–y)Biphenyl–4–yl]Methyl]–1H–Benzimidazole–7–Carboxylate(TCV–116), in Various Hypertensive Rats", Inada et al., *J. Pharmacol. and Experim. Therapeutics.*, vol. 268, No. 3, pp. 1540–1547 (1994).

"Chronic Angiotensin II (AII) Receptor Blockade Lowers Arterial Pressure (AP) and Glomerular Capillary Pressure ($P_{GC}$) in Diabetic Rats" Anderson et al., *American J. of Hypertension,* vol. 4, 11A–12A (1991).

"Non–peptide angiotensin II receptor antagonist and angiotensin–converting enzyme inhibitor: effect on a renin–induced deficit of a passive avoidance response in rats" Denoble et al. *Brain Research,* vol. 561, pp. 230–235 (1991).

"Quantitative Autoradiography Reveals Different Angiotensin II Receptor Subtypes in Selected Rat Brain Nuclei" Tsutsumi et al. *J. of Neurochem.,* vol. 56, No. 1, pp. 348–351 (1991).

"TCV–116 , a Novel Angiotensin II Receptor Antagonist, Prevents Intimal Thickening and Impairment of Vascular Function after Carotoid Injury in Rats" Kawamura et al., *J. Pharmacol. and Experim. Therapeutics,* vol. 266, No. 3, pp. 1664–1669 (1993).

"Effect of an angiotensin II receptor antagonist, CV–11974, and its prodrug, TCV–116, on production of aldosterone" Wada et al., *Eur. J. Pharmacol.,* vol. 253, pp. 27–34 (1994).

"Involvement of the Renin–Angiotensin System in Ischemic Damage and Reperfusion Arrhythmias in the Isolated Perused Rat Heart", Fleetwood et al., *J. Cardiovas. Pharmacol.,* vol. 17, pp. 351–356 (1991).

* cited by examiner

PHARMACEUTICAL COMPOSITION FOR ANGIOTENSIN II-MEDIATED DISEASES

This application is a Divisional of Ser. No. 09/563,855, filed May 4, 2000, which is a Continuation of Ser. No. 09/287,167, filed Apr. 4, 1999, now Abandoned, which is a Divisional of Ser. No. 08/883,040, filed Jun. 26, 1997, now U.S. Pat. No. 5,958,961, which is a Divisional of Ser. No. 08/351,011, filed Dec. 7, 1994, now U.S. Pat. No. 5,721,263, which is a Continuation-in-Part of Ser. No. 08/254,541, filed Jun. 6, 1994, now Abandoned.

FIELD OF THE INVENTION

This invention relates to a pharmaceutical composition for angiotensin II-mediated diseases, which comprises a compound having angiotensin II antagonistic activity or a salt thereof in combination with a compound having diuretic activity or a compound having calcium antagonistic activity, and to a method of its use.

BACKGROUND OF THE INVENTION

Diuretic drugs, due to their having mild hypotensive effects, have long been clinically used as antihypertensive agents. However, as undesirable side effects caused by the use for a long time, influences on metabolism, for example, hypokalemia, hyperuricemia, hyperlipemia and diabetes melitus, have been taken up. While calcium antagonists have been used as therapeutic agents of circulatory diseases such as hypertension, cardiac diseases, cerebral apoplexy, nephritis and arteriosclerosis, it has also been known that they tend to cause such undesirable side effects as tachycardia, hypotension, erythroprosopalgia and encephalagia, which are considered to be due to their abrupt vasodilative action.

On the other hand, it is disclosed in EP-0425921, EP-0459136 and EP-0520423 that benzimidazole derivatives have an angiotensin II antagonistic activities and are useful for the therapy of circulatory diseases including hypertension, cardiac diseases (cardiac insufficiency, myocardial infarction, etc.), cerebral apoplexy, nephritis and arteriosclerosis. The mechanism of the action is considered that the benzimidazole derivatives inhibit the binding of angiotensin II having a strong vasoconstrictive action to an angiotensin II acceptor. And, while, in JPA, H3(1991)-27362 and JPA H5(1993)-132467, it is disclosed that an imidazole derivative having angiotensin II antagonistic action is administered together with a diuretic agent or a calcium antagonistic agent.

OBJECT OF THE INVENTION

The invention is intended, by combination of a compound having angiotensin II antagonistic action or a salt thereof with a compound having diuretic action or a compound having calcium antagonistic activity, to perform especially remarkable effects, to reduce undesirable side effects and to cover up defects observed in administration of a medicine consisting of a single component.

SUMMARY OF THE INVENTION

Circumstances being such as above, the present inventors have made extensive and intensive studies on the effects of co-use of a benzimidazole derivative having angiotensin antagonistic activity with a compound having diuretic activity or a compound having calcium antagonistic activity, and, as a result, they have found that the co-use performs especially remarkable effects which were not observed in the administration of the respective compounds singly, thus accomplishing the present invention.

More specifically, the present invention relates to (1) a pharmaceutical composition for angiotensin II-mediated diseases, which comprises a compound having angiotensin II antagonistic activity of the formula (I):

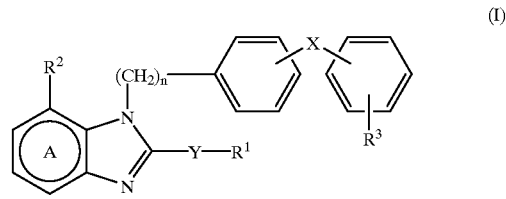

wherein $R^1$ is H or an optionally substituted hydrocarbon residue; $R^2$ is an optionally esterified carboxyl group; $R^3$ is a group capable of forming an anion or a group convertible thereinto; X is a covalent bond between the 2 phenyl rings or a spacer having a chain length of 1 to 2 atoms as the linear moiety between the adjoining phenylene group and phenyl group; n is 1 or 2; the ring A is a benzene ring having 1 or 2 optional substituents in addition to $R^2$; and Y is a bond, —O—, —S(O)m- (wherein m is 0, 1 or 2) or —N($R^4$)— (wherein $R^4$ is H or an optionally substituted alkyl group) or a pharmaceutically acceptable salt thereof in combination with a compound having diuretic activity or a compound having calcium antagonistic activity, and (2) a method for the prophylaxis or treatment of angiotensin II-mediated diseases in a mammal which comprises administering an effective amount of a compound represented by the formula (I) or a pharmaceutically acceptable salt thereof in combination with an effective amount of a compound having diuretic activity or a compound having calcium antagonistic activity.

DETAILED DESCRIPTION OF THE INVENTION

The compounds to be used for the pharmaceutical composition of this invention are those represented by the above-mentioned formula (I). One of the most remarkable structural characteristic of the compounds results when $R^2$ is an optionally esterified carboxyl group and $R^3$ is a group capable of forming anion or a group convertible thereinto. By having such a specific structure as above, the compounds (I) have a very strong angiotensin II antagonistic action.

In formula (I), $R^1$ stands for H or an optionally substituted hydrocarbon residue.

Examples of the hydrocarbon residue represented by $R^1$ include alkyl, alkenyl, alkynyl, cycloalkyl, aryl and aralkyl groups. Among them alkyl, alkenyl and cycloalkyl groups are preferable.

The alkyl group represented by $R^1$ is a straight chain or branched lower alkyl group having 1 to about 8 carbon atoms, as exemplified by methyl, ethyl, propyl, isopropyl, butyl, isobutyl, sec-butyl, t-butyl, pentyl, i-pentyl, hexyl, heptyl or octyl.

The alkenyl group represented by $R^1$ is a straight chain or branched lower alkenyl group having 2 to about 8 carbon atoms, as exemplified by vinyl, propenyl, 2-butenyl, 3-butenyl, isobutenyl or 2-octenyl.

The alkynyl group represented by $R^1$ is a straight chain or branched lower alkynyl group having 2 to about 8 carbon atoms, as exemplified by ethynyl, 2-propinyl, 2-butynyl, 2-pentynyl or 2-octynyl.

The cycloalkyl group represented by $R^1$ is a lower cycloalkyl group having 3 to about 6 carbon atoms, as exemplified by cyclopropyl, cyclobutyl, cyclopentyl or cyclohexyl.

The above mentioned alkyl, alkenyl, alkynyl or cycloalkyl group may optionally be substituted with hydroxyl group, an optionally substituted amino group (e.g. amino, N-lower $(C_{1-4})$ alkylamino or N,N-dilower $(C_{1-4})$ alkylamino), halogen, a lower $(C_{1-4})$ alkoxy group, a lower $(C_{1-4})$ alkylthio group.

The aralkyl group represented by $R^1$ is, for example, a phenyl-lower $(C_{1-4})$ alkyl such as benzyl or phenethyl, and the aryl group represented by $R^1$ is, for example, phenyl.

The above mentioned aralkyl or aryl group may optionally have, on any position of its benzene ring, for example, halogen (e.g. F, Cl or Br), nitro, an optionally substituted amino group (e.g. amino, N-lower $(C_{1-4})$ alkylamino or N,N-dilower $(C_{1-4})$ alkylamino), lower $(C_{1-4})$ alkoxy (e.g. methoxy or ethoxy), lower $(C_{1-4})$ alkylthio (e.g. methylthio or ethylthio) or lower $(C_{1-4})$ alkyl (e.g. methyl or ethyl).

Among the above mentioned groups represented by $R^1{}_1$, optionally substituted alkyl, alkenyl or cycloalkyl groups (e.g. a lower $(C_{1-5})$ alkyl, lower $(C_{2-5})$ alkenyl or lower $(C_{3-6})$ cycloalkyl group optionally substituted with hydroxyl group, amino group, halogen or a lower $(C_{1-4})$ alkoxy group) are preferable.

Y stands for a bond, —O—, —S(O)m- (wherein m is 0, 1 or 2) or —N(R$^4$)— (wherein R$^4$ is hydrogen or an optionally substituted lower alkyl group). Y is preferably a bond, —O—, —S— or —N(R$^4$)— (wherein R$^4$ is hydrogen or a lower $(C_{1-4})$ alkyl group (e.g. methyl, ethyl, propyl, isopropyl, butyl, sec-butyl, t-butyl)).

With respect to formula (I) above, the group for $R^3$, capable of forming an anion (a group having a hydrogen atom capable of leaving as a proton), or a group capable of changing thereto, is exemplified by 5- to 7- membered (preferably 5- or 6- membered) monocyclic heterocyclic ring residues which contain one or more of N, S and O and which may be substituted (preferably N-containing heterocyclic residues having a hydrogen atom capable of leaving as a proton), and groups capable of changing thereto in vivo. Such groups include the following:

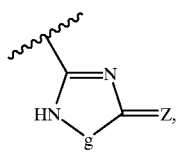
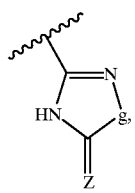
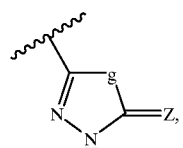

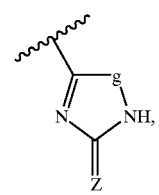
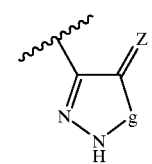
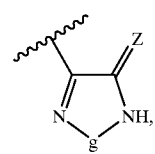

-continued

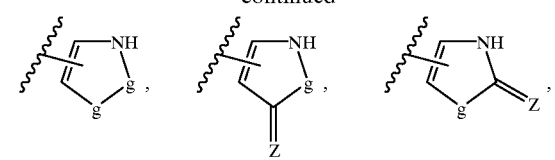

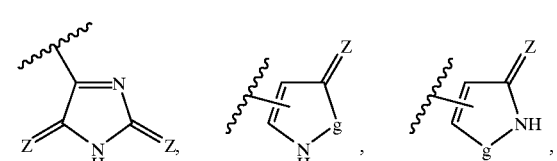

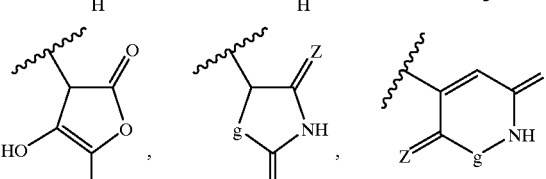

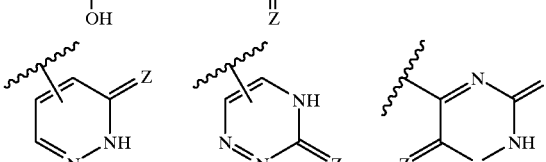

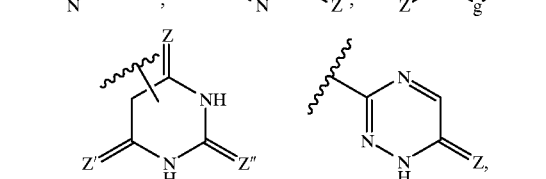

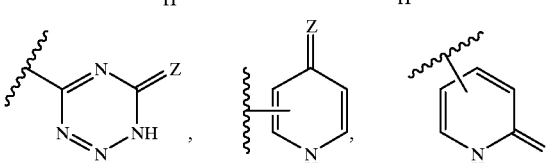

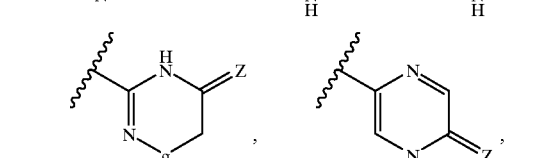

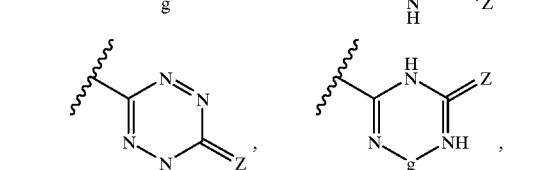

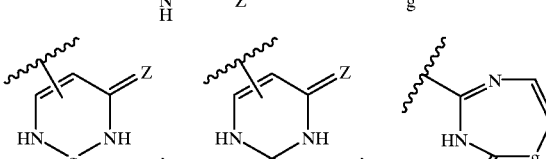

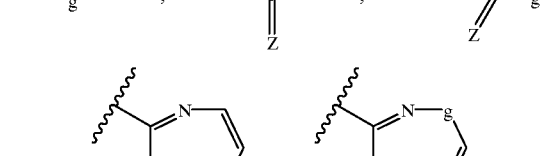

The chemical bond between the group for $R^3$ and the partner phenyl group may be a carbon-carbon bond as shown above, or a nitrogen-carbon bond via one of the several nitrogen atoms when the symbol g stands for —NH— in the above formulas. For instance, when $R^3$ is represented by

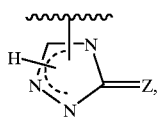

embodiments are

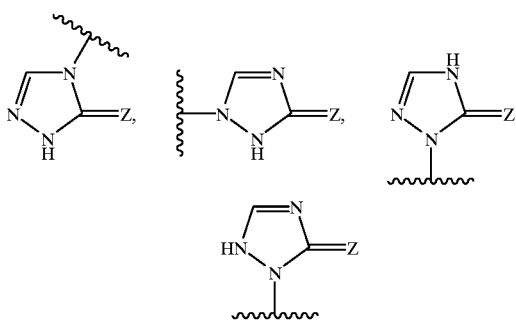

Other $R^3$ examples binding through the nitrogen atom are

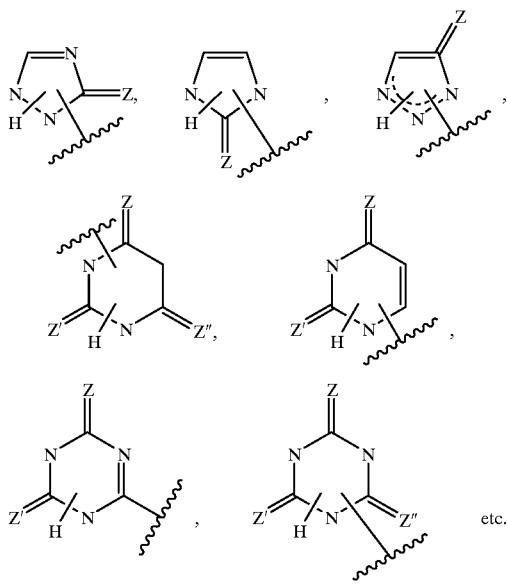

In the above groups, g stands for —CH$_2$—, —NR$^7$—, oxygen atom, or

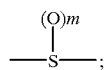

>=Z, >=Z' and >=Z" each stand for a carbonyl group, a thiocarbonyl group or an optionally oxidized sulfur atom (e.g., S, S(O), S(O)$_2$) (preferably, a carbonyl or thiocarbonyl group; more preferably, a carbonyl group); m stands for the integer 0, 1 or 2; $R^7$ stands for a hydrogen atom or an optionally substituted lower alkyl group (e.g. a lower (C$_{1-4}$) alkyl group (e.g. methyl, ethyl, propyl, isopropyl, butyl, sec-butyl, t-butyl)).

Preferable examples of $R^3$ include 2,5-dihydro-5-oxo-1, 2,4-oxadiazole ring residue, 2,5-dihydro-5-thioxo-1,2,4-oxadiazole ring residue or 2,5-dihydro-5-oxo-1,2,4-thiadiazole ring residue having —NH or —OH group as proton donor and carbonyl group, thiocarbonyl group or sulfinyl group as proton acceptor simultaneously.

And, while the heterocyclic residue represented by $R^3$ may form a condensed ring by connecting the substituents on the ring, it is preferably a 5- to 6-membered ring, more preferably a 5-membered heterocyclic residue. Especially, groups represented by the formula

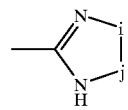

wherein i stands for —O— or —S—; j stands for >C=O, >C=S or >S(O)m; m stands for the integer 0, 1 or 2 (in particular, 2,5-dihydro-5-oxo-1,2,4-oxadiazole-3-yl; 2,5-dihydro-5-thioxo-1,2,4-oxadiazole-3-yl; 2,5-dihydro-5-oxo-1,2,4-thiadiazole-3-yl) are preferable. $R^3$ can be substituted at the ortho, meta or para position of the phenyl group, most preferably at the ortho position.

In addition, the above-mentioned heterocyclic residue ($R^3$) have the following tautomeric isomers:

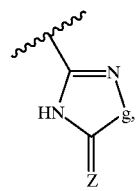

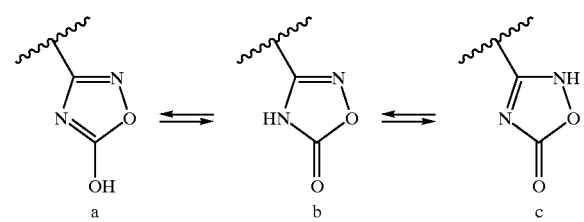

the three tautomeric isomers a, b and c exist.

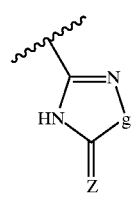

The heterocyclic residue represented by the above formula comprises all of these a, b and c.

Moreover, $R^3$ may be a carboxyl group, tetrazolyl group, trifluoromethanesulfonamide group (—NHSO$_2$CF$_3$). phosphate group, sulfonic group, cyano group, or lower (C$_{1-4}$) alkoxycarbonyl group; these groups each may be protected by an optionally substituted lower alkyl or acyl group. Any group capable of forming an anion biologically or physiologically (e.g. through biological reactions such as oxidation, reduction or hydrolysis caused by enzymes in the body) or chemically, or a group capable of changing thereto is acceptable.

As $R^3$, a tetrazolyl or carboxyl (preferably tetrazolyl) group optionally protected by an optionally substituted lower ($C_{1-4}$) alkyl (e.g., methyl, triphenylmethyl, methoxymethyl, ethoxymethyl, p-methoxybenzyl, p-nitrobenzyl, etc.) or acyl (e.g., lower ($C_{2-5}$) alkanoyl, benzoyl, etc.) group is preferable. $R^3$ can be replaced at the ortho, meta or para position of the phenyl group, most preferably at the ortho position.

X stands for a covalent bond between the 2 phenyl rings or a spacer having a chain length of 1 to 2 atoms as the linear moiety between the adjoining phenylene group and phenyl group. Preferably, X is a covalent bond. The spacer having a chain length of 1 to 2 atoms may consist of a divalent chain in which the number of atoms composing the straight chain portion is either 1 or 2, and may have a side chain. For example, a lower ($C_{1-4}$) alkylene, —CO—, —O—, —S—, —NH—, —CO—NH—, —O—CH$_2$—, —S—CH$_2$—, —CH=CH—, etc. are listed.

n stands for the integer 1 or 2 (preferably 1).

The formula represented by the above-mentioned $R^3$, X and n:

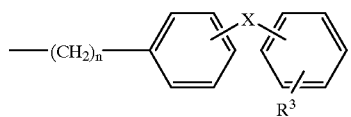

is preferably represented by the formula:

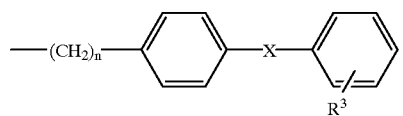

$R^2$ in formula (I) is an optionally esterified carboxyl group.

The optionally esterified carboxyl group as $R^2$ includes the group represented by the formula —CO—D (wherein D stands for a hydroxyl group or an optionally substituted alkoxyl group (e.g., a lower ($C_{1-6}$) alkoxyl group whose alkyl portion is optionally substituted with a hydroxyl, optionally substituted amino (e.g., amino, dimethylamino, diethylamino, piperidino, molphorino, etc.), halogen, lower ($C_{1-6}$) alkoxyl, lower ($C_{1-6}$) alkylthio or optionally substituted dioxolanyl (e.g., 5-methyl-2-oxo-1,3-dioxolane-4-yl, etc.) group, or the group represented by the formula —O—CH($R^6$)—OCOR$^5$ [wherein $R^6$ stands for H, a lower ($C_{1-6}$) straight chain or branched alkyl group (e.g., methyl, ethyl, n-propyl, isopropyl, n-butyl, isobutyl, t-butyl, n-pentyl, isopentyl neopentyl, etc.), a lower ($C_{2-6}$) straight chain or branched alkenyl group or a lower ($C_{3-8}$) cycloalkyl group (e.g., cyclopentyl, cyclohexyl, cycloheptyl, etc.); $R^5$ stands for a lower ($C_{1-6}$) straight chain or branched alkyl group (e.g., methyl, ethyl, n-propyl, isopropyl, n-butyl, isobutyl, sec-butyl, t-butyl, n-pentyl, isopentyl, neopentyl, etc.), a lower ($C_{2-6}$) straight chain or branched alkenyl group, a lower ($C_{3-8}$) cycloalkyl group (e.g., cyclopentyl, cyclohexyl, cycloheptyl, etc.), a lower ($C_{1-3}$) alkyl group substituted with $C_{3-8}$ cycloalkyl (e.g. cyclopentyl, cyclohexyl, cycloheptyl) or an optionally substituted aryl group such as phenyl group (e.g., benzyl, p-chlorobenzyl, phenetyl, cyclopentylmethyl, cyclohexylmethyl, etc.), a lower ($C_{2-3}$) alkenyl group optionally substituted with $C_{3-8}$ cycloalkyl or an optionally substituted aryl group such as phenyl (e.g., cinnamyl, etc. having alkenyl moiety such as vinyl, propenyl, allyl and isopropenyl, etc.), an aryl group such as optionally substituted phenyl (e.g., phenyl, p-tolyl, naphtyl, etc.), a lower ($C_{1-6}$) straight chain or branched alkoxyl group (e.g., methoxyl, ethoxyl, n-propoxyl, isopropoxyl, n-butoxyl, isobutoxyl, sec-butoxyl, t-butoxyl, n-pentyloxyl, isopentyloxyl, neopentyloxyl, etc.), a lower ($C_{2-8}$) straight chain or branched alkenyloxyl group (e.g., allyloxyl, isobutenyloxyl, etc.), a lower ($C_{3-8}$) cycloalkyloxyl group (e.g., cyclopentyloxyl, cyclohexyloxyl, cycloheptyloxyl, etc.), a lower ($C_{1-3}$) alkoxyl group substituted with a $C_{3-8}$ cycloalkyl (e.g., cyclopentyl, cyclohexyl, cycloheptyl, etc.) or anaryl group such as optionally substituted phenyl (e.g., benzyloxy, phenethyloxy, cyclopentylmethyloxy and cyclohexylmethyloxy having alkoxy moiety such as methoxy, ethoxy, n-propoxy and isopropoxy), a lower ($C_{2-3}$) lower alkenyloxy group substituted with a $C_{3-8}$ cycloalkyl (e.g., cyclopentyl, cyclohexyl, cycloheptyl, etc.) or an optionally substituted aryl group such as phenyl group (e.g., cinnamyloxy etc. having alkenyloxy moiety such as vinyloxy, propenyloxy, allyloxy, isopropenyloxy, etc.), or an optionally substituted aryloxyl group such as phenoxyl (e.g., phenoxyl, p-nitrophenoxyl, naphtoxyl, etc.,)}]. The substituent for $R^2$ may be a group actually or potentially capable of forming an anion (e.g., tetrazolyl group, trifluoromethanesulfonamide group, phosphate group or sulfonic group optionally protected by an alkyl {e.g., lower ($C_{1-4}$) alkyl, etc.} or acyl {e.g., lower ($C_{2-5}$) alkanoyl, optionally substituted benzoyl, etc.} group]. For example, the following substituents are listed: COOH and its salts, —COOMe, —COOEt, —COOtBu, —COOPr, pivaloyloxymethoxycarbonyl, 1-(cyclohexyloxycarbonyloxy)ethoxycarbonyl, (5-methyl-2-oxo-1,3-dioxolane-4-yl)methoxycarbonyl, acetoxymethoxycarbonyl, propionyloxymethoxycarbonylr n-butylyloxymethoxycarbonyl, isobutylyloxymethoxycarbonyl, 1-(ethoxycarbonyloxy)ethoxycarbonyl, 1-(acetoxy)ethoxycarbonyl, 1-(isobutylyloxy)ethoxycarbonyl, cyclohexylcarbonyloxymethoxycarbonyl, benzoyloxymethoxycarbonyl, cinnamiloxycarbonyl and cyclopentylcarbonyloxymethoxycarbonyl, etc.. Furthermore, $R^7$ may be any of the groups actually or potentially capable of forming an anion (e.g., COO— or its derivatives, etc.) under biologic or physiologic conditions (e.g., oxidation or reduction induced by an enzyme present in the living body; in vivo reaction such as hydrolysis) or chemically. $R^2$ may also be a carboxyl group or its prodrug. $R^2$ may be a group capable of being biologically or chemically biotransformed to an anion.

Among the groups described as $R^2$, preferable ones include carboxyl, esterified carboxyl (e.g., methyl ester, ethyl ester or an ester formed by binding of a group represented by the above mentioned formula —O—CH($R^6$)—OCOR$^5$ to carbonyl) and optionally protected tetrazolyl, carboaldehyde and hydroxymethyl.

In general formula (I), ring A may have, in addition to the group represented by $R^2$, another substituent, e.g., a halogen atom (e.g., F, Cl, Br, etc.), cyano group, nitro group, lower ($C_{1-4}$) alkyl group, lower ($C_{1-4}$) alkoxyl group, optionally substituted amino group {e.g., amino, N-lower ($C_{1-4}$) alkylamino (e.g., methylamino, etc.), N,N-dilower ($C_{1-4}$) alkylamino (e.g., dimethylamino, etc.), N-arylamino (e.g., phenylamino, etc.), alicyclic amino (e.g., morpholino, piperidino, piperazino, N-phenylpiperazino, etc.), etc.}, a group represented by the formula —CO—D' [wherein D' stands for a hydroxyl group or a lower ($C_{1-4}$) alkoxyl group whose alkyl moiety may be substituted with a hydroxyl group, lower ($C_{1-4}$) alkoxyl group, lower ($C_{2-6}$) alkanoyloxy (e.g., acetoxyl, pivaloyloxyl, etc.) or lower ($C_{1-6}$) alkoxycarbonyloxyl (e.g., methoxycarbonyloxyl, ethoxycarbonyloxy, cyclohexyloxycarbonyloxy, etc.) group], or tetrazolyl, trifluoromethanesulfonamide, phosphoric acid or sulfonic acid group which may be protected by lower ($C_{1-4}$) alkyl or acyl group (e.g., lower ($C_{2-5}$) alkanoyl, optionally substituted benzoyl, etc.); among them, a lower ($C_{1-4}$) alkyl group and a halogen group are preferable. Of these substituents, one or two may simultaneously substitute for groupsat available positions in the ring.

Among the compounds represented by the above mentioned formula (I), compounds represented by formula (I') are preferred:

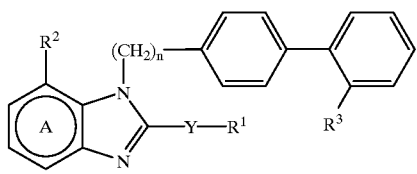

(I')

[wherein ring A stands for a benzene ring which may have another 1 or 2 substituents in addition to the group represented by $R^2$; $R^1$ stands for H or an optionally substituted lower ($C_{1-6}$) alkyl (preferably lower ($C_{1-4}$) alkyl); Y stands for O, N(H) or S; $R^2$ is a group represented by the formula —CO—D" (wherein D" stands for hydroxyl group, or a lower ($C_{1-4}$) alkoxy whose alkyl moiety is optionally substituted with hydroxyl group, amino, halogen, a lower ($C_{2-6}$) alkanoyloxy (e.g. acetyloxy and pivaloyloxy, etc.), lower ($C_{4-7}$) cycloalkanoyloxy, lower ($C_{1-6}$) alkoxycarbonyloxy (e.g. methoxycarbonyloxy, ethoxycarbonyloxy), lower ($C_{3-7}$) cycloalkoxycarbonyloxy (e.g. cyclohexyloxycarbonyloxy) or a lower ($C_{1-4}$) alkoxy; $R^3$ stands for a tetrazolyl, carboxyl group or groups represented by the formula,

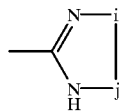

wherein i stands for —O— or —S—; j stands for >C=O, >C=S or >S(O)$_m$; and m stands for the integer 0, 1 or 2, which are optionally protected with optionally substituted lower ($C_{1-4}$) alkyl (e.g. methyl, triphenylmethyl, methoxymethyl, acetyloxymethyl, methoxycarbonyloxymethyl, ethoxycarbenyloxymethyl, 1-(cyclohexyloxycarbonyloxy)ethyl and pivaloyloxymethyl, etc.) or an acyl group (e.g. a lower $C_{2-5}$ alkanoyl and benzoyl, etc.); n is 1 or 2.

In the formula (I'), substituents on the optionally substituted lower alkyl for $R^1$ include a hydroxyl group, an amino group, halogen and a lower ($C_{1-4}$) alkoxy group.

In the formula (I'), ring A is a benzene ring which may have a substituent, in addition to the group $R^2$, such as a halogen (e.g., F, Cl, Br), lower ($C_{1-4}$) alkyl, lower ($C_{1-4}$) alkoxy, nitro, a group represented by the formula —CO—D', wherein D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyloxy, etc.) or lower ($C_{1-6}$) alkoxycarbonyloxy (e.g., methoxycarbonyloxy, ethoxycarbonyloxy, cyclohexyloxycarbonyloxy), or an amino which may be substituted with a lower ($C_{1-4}$) alkyl (preferably a substituent such as a lower ($C_{1-4}$) alkyl or halogen). More preferably, A is a benzene ring which has no substituent in addition to the group represented by the formula $R^2$.

As the salt thereof, pharmaceutically acceptable salts are used, e.g., a salt with an inorganic base, organic base, inorganic acid, organic acid, or basic or acidic amino acid. Inorganic bases appropriate to form the salt include alkali metals such as sodium or potassium, alkali earth metals such as calcium and magnesium or aluminum, and ammonia. Organic bases appropriate to form the salt include trimethylamine, triethylamine, pyridine, picoline, ethanolamine, dietanolamine, triethanolamine, dicyclohexylamine, and N,N'-dibenzylethylenediamine. Inorganic acids appropriate to form the salt include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

As an active ingredient of the present invention, the compounds having angiotensin II antagonistic activity described in the Examples of Japan Provisional Publication No. 364171/1992 and EP520423 are preferred. The compounds represented by general formula (I) were, for instance, disclosed in Provisional Publication Nos. 9373/1992 and 364171/1992, and EP520423, and can be manufactured as described in these publications.

As compounds having diuretic activity, while mention is made of amiloride, chlorothiazide, hydrochloride, benzthiazide, ticrynafen, acetazolamide, aminophylline, cyclothiazide, trichloromethiazide, cyclopenthiazide, hydrochlorothiazide, methyclothiazide, benzylhydrochlorothiazide, penfluthiazide, ethiazide, hydroflumethiazide, polythiazide, clofenamide, chlorthalidone, cyclothiazide, bendroflumethiazide, meticrane, tripamide, methrazone, indapamide, quinethazone, furosemide, bumetanide, mefruside, azosemide, ethacrynic acid, sodium ethacrynate, piretanide, spironolactone, potassium canrenoate and triamterene, mention is also made of a mixture of them or a combination of them.

As compounds having calcium antagonistic activity, while mention is made of diltiazem hydrochloride, terodiline hydrochloride, nicardipine hydrochloride, valnidipine hydrochloride, flunarizin hydrochloride, varapamyl hydrochloride, manidipine hydrochloride, cinnarizine, nisoldipine, nitrendipine, nifedipine, nilvadipine, felodipine, nildipine, nimodipine, penidipine and-benidipine; mention is also made of a mixture of them or a combination of them.

The angiotensin II mediated diseases include hypertension, cardiac insufficiency, ischemic peripheral circulation disturbances, myocardial ischemia, vein insufficiency, progressive cardiac insufficiency after myocardial infarction, diabetic nephritides, nephritis, arteriosclerosis, hyperaldosteronism, dermatosclerosis, glomerulosclerosis, renal insufficiency, diseases of central nervous system, sensory disturbances including Alzheimer's disease, deficiency of memory, depression, amnesia and senile dementia, anxiety neurosis, catatonia or indisposition, glaucoma, intraocular high tension.

The pharmaceutical composition of angiotensin II-mediated diseases, whose effective components being a compound having angiotensin II antagonistic activity represented by the formula (I) compound or a salt thereof and a compound having diuretic activity or a compound having calcium antagonistic activity, can be administered orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like. In the case of formulating the effective components individually, while thus individually formulated agents can be administered in the form of their mixture prepared by using, for example, a diluent when administered, the individually formulated agents can also be administered separately or simultaneously or with time intervals to the one and same subject.

The pharmaceutical composition for angiotensin II-mediated diseases of the present invention can be formulated in accordance with conventional procedures. In the present specification, "non-orally" include subcutaneous injection, intravenous injection, intramuscular injections, intraperitoneal injection or instillation. Injectable preparations, for example, sterile injectable aqueous suspensions or oil suspensions can be prepared by known procedure in the fields concerned, using a suitable dispersant or wetting agent and suspending agent. The sterile injections may be in the state of, for example, a solution or a suspension, which is prepared with a non-toxic diluent administrable non-orally, e.g. an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent.

Any non-volatile oil and a fatty acid can be used for this purpose, which includes natural or synthetic or semi-synthetic fatty acid oil or fatty acid, and natural or synthetic or semi-synthetic mono- or di- or tri-glycerides.

Rectal suppositories can be prepared by mixing the drug with a suitable non-irritable vehicle, for example, cocoa butter and polyethylene glycol, which is in the solid state at ordinary temperatures, in the liquid state at temperatures in intestinal tubes and melts in rectum to release the drug.

As a solid formulation for oral administration, mention is made of powders, granules, tablets, pills and capsules as referred to in the above. In such formulations as exemplified above, the active component compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, α-tocopherol or cysteine, a disintegrator, a binder, a thickening agent, a buffer, a sweetener, a flavoring agent and a perfuming agent. Tablets and pills can further be prepared with enteric coating. Examples of liquid preparations for oral administration include pharmaceutically acceptable emulsions, syrups, elixirs, suspensions and solutions, which may contain an inactive diluent, for example, water, which is conventionally employed in the field concerned.

The pharmaceutical composition of this invention against angiotensin II-mediated diseases are less toxic, which is used as a medicine for animals, especially mammals (e.g. human being, dog, rabbit, mouse, etc.), can be advantageously used for angiotensin II-mediated diseases.

The pharmaceutical composition of this invention for angiotensin II-mediated diseases formulated by combining a compound having angiotensin II antagonistic activity or a salt thereof with a-compound having diuretic activity or a compound having calcium antagonistic activity. This composition serves to decrease the dosages of the individual effective components, and, as a result, suppresses undesirable side effects observed in the case of administering the respective compounds singly.

Also, by incorporation of polymers of alkylene oxide into a formulation comprising a compound having angiotensin II antagonistic activity represented by the formula (I), or a salt thereof and a compound having diuretic activity or a compound having calcium antagonistic activity, decomposition of the active components is remarkably suppressed to afford a stable composition.

The above polymers of alkylene oxide may be evenly admixed with the active components in preparation of pharmaceutical. compositions for oral use so that more stable compositions are produced. Furthermore, among the polymers of alkylene oxide, any one may be soluble or insoluble in water.

As the polymer of alkylene oxide, use is made of those having a molecular weight of 1,000 to 10,000 (e.g. polyethylene glycol 6000). Examples of the alkylene oxide include ethylene oxide, propylene oxide, trimethylene oxide and tetrahydrofuran (preferably ethylene oxide).

The polymers of alkylene oxide may be used singly or as a mixture of two or more of them.

The polymers are added to the active components in a solid or liquid state.

The method for preparing a pharmaceutical composition using polymers of alkylene oxide is more conveniently applied to a solid composition (e.g., granules and tablets, preferably tablets) prepared by molding (e.g. granulation or molding under elevated pressure).

Preparation of a solid composition is usually conducted by incorporating polymers of alkylene oxide into the active components, followed by subjecting the mixture to molding. The incorporation is conducted by a method conventionally employed in the field of pharmaceutical preparations, for example, mixing, massing, kneading, sieving and stirring. For example, polymers of alkylene oxide are directly added to the active components and to make a mixture (addition in powdery state), or a solvent is added to the mixture, followed by conventional granulating and drying. Alternatively, polymers of alkylene oxide are dissolved in a suitable solvent, then the solution is mixed with the active components, followed by conventional kneading, granulating and drying (addition in liquid state). Further, a liquid material containing polymers of alkylene oxide and a liquid material containing the active components can be independently sprayed onto a powdery material such as an excipient, followed by mixing the resultant material. In the case of "addition in liquid state", any solvent which does not exert undesirable influence on the active component, for example, water, dimethylformamide, acetone, ethanol, propyl alcohol, isopropyl alcohol, butyl alcohol, methylene chloride and trichloroethane, can be employed. After completing the blending, the material is subjected to a conventional molding process under elevated pressure to prepare tablets containing the active components. The molding under elevated pressure means that a material is compressed under elevated pressure into a desired form, and it refers to, most generally, tabletting. Incorporation or polymers of alkylene oxide as described above serves to minimize crystalline disorder possibly caused in the steps of kneading, granulating and molding under elevated pressure and is considered to further serve advantageously to improve the moldability and to lower the pressure to be elevated. In the method of preparing the composition, a variety of additives to be employed for solid compositions can be added in an adequate step. These additives are exemplified by excipients such as crystalline cellulose (e.g. Avicel PH 101 (manufactured by Asahi Chemical Industry Co., Ltd.), carboxymethyl cellulose calcium, corn starch, wheat starch, lactose, sucrose, glucose, calcium sulfate, calcium phosphate or sodium chloride, binders such as gum arabic, gelatin, methyl cellulose, polyvinyl pyrrolidone, hydroxypropyl cellulose (hereinafter sometimes abbreviated as HPC) or hydroxypropylmethyl cellulose, lubricants such as magnesium stearate, talc, synthetic aluminum silicate, sodium lauryl sulfate, boric acid, magnesium oxide or paraffin, colorants, flavoring agents, odor-improving agents, etc. Furthermore, the composition may be prepared into coated tablets as well.

The coating process may be accomplished by a known method. Use is made of conventional coating agents (e.g., hydroxy-propylmethyl cellulose, hydroxypropyl cellulose, methyl cellulose and polyvinyl pyrrolidone). Polyethylene glycol 6000, polysorbate, titanium oxide and pigments such as red iron oxide are used as auxiliary agents for coatings.

In the stabilized pharmaceutical composition for oral use prepared by admixing polymers of alkylene oxide with the active components, the amount of the polymers is 0.005 to 0.15 weight, preferably 0.01 to 0.1 weight, preferably 0.02 to 0.05 weight per 1 weight of the composition.

The dose of a specific patient is dependent on the age, body weight, general health conditions, sex, diet, dose interval, administration routes, excretion rate, combinations of drugs and conditions of the diseases treated, while taking these and other necessary factors into consideration.

Typical daily doses of the compositions having various combinations of a compound represented by the formula (I) or a salt thereof and a compound having diuretic activity or a compound having calcium antagonistic activity are within the range of from about 1/50 of the minimal recommendable clinical dose to maximal recommendable dose in the case of practical administration of these compounds individually.

For example, a compound represented by the formula (I) having an angiotensin II antagonistic activity to be administered at a dose of about 0.01 to 150 mg/patient/day can be administered at a dose of about 0.0002 to 150 mg/patient/day, preferably 0.001 to 60 mg/patient/day, more preferably 0.01 to 20 mg/patient/day by combining with the following daily doses of the following compounds: trichloromethiazide (1 to 8 mg), cyclopenthiazide (0.25 to 1 mg), cyclothiazide (1 to 2 mg), chlorothiazide (500 to 1000 mg), bendroflumethiazide (2 to 10 mg), hydrochlorothiazide (5 to 200 mg), methyclothiazide (2.5 to 5 mg), benzylhydrochlorothiazide (4 to 16 mg), penfluthiazide (1.5 to 7.5 mg), ethiazide (2.5 to 10 mg), hydroflumethiazide (10 to 200 mg), polythiazide (0.25 to 4 mg), meticrane (150 to 300 mg), chlorothalidone (50 to 200 mg), tripamide (15 to 30 mg), methrazone (2.5 to 5 mg), indapamide (0.5 to 2 mg), quinethazone (25 to 150 mg), clofenamide (50 to 400 mg), furosemide (20 to 500 mg), bumetanide (0.5 to 2 mg), mefruside (1.25 to 50 mg), diltiazem hydrochloride (10 to 200 mg), nicardipine hydrochloride (3 to 40 mg), valnidipine hydrochloride (2 to 15 mg), flunarizine hydrochloride (2 to 10 mg), verapamil hydrochloride (2 to 80 mg), manidipine hydrochloride (2 to 20 mg), cinnarizine (10 to 50 mg), nisoldipine (2 to 10 mg), nitrendipine (2 to 10 mg), nifedipine (3 to 40 mg), nilvadipine (1 to 8 mg), or benidipine (2 to 8 mg). Needless to say, while these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration.

The desired unit dose of the composition of this invention is administered once or twice daily (preferably once).

For example, the unit dose composition contains about 0.0002 to 150 mg, preferably 0.001 to 60 mg, more preferably 0.01 to 20 mg of a compound represented by the formula (I) by combining with the following amount of the following compound: trichloromethiazide (1 to 8 mg), cyclopenthiazide (0.25 to 1 mg), cyclothiazide (1 to 2 mg), chlorothiazide (500 to 1000 mg), bendroflumethiazide (2 to 10 mg), hydrochlorothiazide (5 to 200 mg), methyclothiazide (2.5 to 5 mg), benzylhydrochlorothiazide (4 to 16 mg), penfluthiazide (1.5 to 7.5 mg), ethiazide (2.5 to 10 mg), hydroflumethiazide (10 to 200 mg), polythiazide (0.25 to 4 mg), meticrane (150 to 300 mg), chlorothalidone (50 to 200 mg), tripamide (15 to 30 mg), methrazone (2.5 to 5 mg), indapamide (0.5 to 2 mg), quinethazone (25 to 150 mg), clofenamide (50 to 400 mg), furosemide (20 to 500 mg), bumetanide (0.5 to 2 mg), mefruside (1.25 to 50 mg), diltiazem hydrochloride (10 to 200 mg), nicardipine hydrochloride (3 to 40 mg), valnidipine hydrochloride (2 to 15 mg), flunarizine hydrochloride (2 to 10 mg), verapamil hydrochloride (2 to 80 mg), manidipine hydrochloride (2 to 20 mg), cinnarizine (10 to 50 mg), nisoldipine (2.to 10 mg), nitrendipine (2 to 10 mg), nifedipine (3 to 40 mg.), nilvadipine (1 to 8 mg), or benidipine (2 to 8 mg).

The composition of this invention as described above is advantageously carried out in combination with hydrochlorothiazide. The amount of hydrochlorothiazide present in a dosage unit is from about 5 mg to 200 mg, preferably 5 mg to 100 mg, more preferably 5 to 50 mg.

By the following test examples and working examples, the present invention will be illustrated in more detail, and they should not be construed as limiting the invention thereto.

The physiological activities of the composition comprising a compound having angiotensin II 11 antagonistic activity or a salt thereof and a compound having diuretic activity or a compound having calcium antagonistic activity are described by the following test examples.

TEST EXAMPLE 1

Antihypertensive Activity in Spontaneously Hypertensive Rats (SHR) by the Co-administration with a Diuretic Drug Compound 1: (±)-1-(cyclohexyloxycarbonyloxy) ethyl 2-ethoxy-1-[[2'-(1H-tetrazol-5-yl)biphenyl-4-yl]methyl]-1H-benzimidazole-7-carboxylate HCT: hydrochlorothiazide Method: Male SHR of 20 week old were divided into 6 groups (five animals in one group). The respective groups were administered orally with the compound 1(0.1 or 1 mg/kg,p.o.) or HCT (10 mg/kg, p.o.) alone or both drugs simultaneously once a day for two weeks. On the first, 7th and 14th day at 5 hr after the administration, blood pressure of each test animal was measured by the tail cuff method under unanesthesia.

Results: As shown in Table 1. Single dose of HCT (10 mg/kg/day, p.o.) did not show antihypertensive action. The compound 1 (0.1 and 1 mg/kg/day) showed dose dependent antihypertensive action. Efficiency of the antihypertensive activity of the compound 1 was enhanced by its co-administration with HCT. The antihypertensive activity observed by the combination of the compound 1 (0.1 mg/kg) and HCT was stronger or substantially the same as that observed by administering the compound 1 alone (1 mg/kg). This result shows that the combination of both drugs can decrease the dosages of the respective drugs.

TABLE 1

Antihypertensive activity by the combination of compound 1 and the diuretic drug in spontaneously hypertensive rats

| Test group (dosage) mg/kg/day, p.o. | Before admin. | 1 day | 1 week | 2 weeks |
|---|---|---|---|---|
| | | (blood pressure: mmHg) | | |
| Control — | 183 ± 2 | 183 ± 1 | 179 ± 2 | 181 ± 4 |
| HCT (10) | 186 ± 3 | 178 ± 3 | 177 ± 3 | 181 ± 2 |
| Cpd. 1 (0.1) | 183 ± 2 | 161 ± 5 | 155 ± 3 | 162 ± 3 |
| Cpd. 1 (1) | 186 ± 2 | 153 ± 5 | 138 ± 2 | 135 ± 3 |
| HCT (10) + Cpd. 1 (0.1) | 186 ± 4 | 137 ± 5 | 129 ± 5 | 139 ± 3 |
| HCT (10) + Cpd. 1 (1) | 187 ± 2 | 132 ± 3 | 106 ± 5 | 108 ± 4 |

Numerical values: average values ± standard error

TEST EXAMPLE 2

Antihypertensive Activity in Spontaneously Hypertensive Rats (SHR) by the Co-administration with a Calcium Antagonistic Drug Compound 1: (±)-1-(cyclohexyloxycarbonyloxy) ethyl 2-ethoxy-1-[[2'-(1H-tetrazol-5-yl)biphenyl-4-yl]methyl]-1H-benzimidazole-7-carboxylate MDP: manidipine Method: Male SHR of 20 week old were divided into six groups (five animals per group). The respective groups were administered orally with the compound 1 (0.1 or 1 mg/kg, p.o.) or MDP (3 mg/kg, p.o.) alone or with a mixture of them once a day for two weeks. On the first, 7th and 14th day at 5 hr after the administration, blood pressure of each test animal was measured by the tail cuff method under unanesthesia.

Results.: As shown in Table 2. Single administration of MDP (3 mg/kg/day, p.o.) showed apparent antihypertensive effect, and the compound 1 (0.1 and 1 mg/kg/day) performed dose dependent antihypertensive effect. The antihypertensive activity of the compound 1 was enhanced by the co-administration with MDP (3 mg/kg/day). The hypotensive activity observed by the co-administration of the compound 1 (0.1 mg/kg) with MDP was stronger or substantially the same as that observed by administering the compound 1 alone (1 mg/kg). This result shows that simultaneous usage of both drugs can decrease in the dosages of the respective drugs.

TABLE 2

Antihypertensive activity by the combination of compound 1 and the calcium antagonistic drug in spontaneously hypertensive rats

| Test group (dosage) mg/kg/day, p.o. | Before admin. | 1 day | 1 week | 2 weeks |
|---|---|---|---|---|
| | | (blood pressure: mmHg) | | |
| Control — | 188 ± 3 | 184 ± 2 | 181 ± 3 | 179 ± 1 |
| MDP (3) | 190 ± 5 | 157 ± 2 | 132 ± 5 | 136 ± 7 |
| Cpd. 1 (0.1) | 190 ± 2 | 157 ± 2 | 158 ± 4 | 160 ± 4 |
| Cpd. 1 (1) | 196 ± 3 | 148 ± 3 | 131 ± 13 | 142 ± 4 |
| MDP (3) + Cpd. 1 (0.1) | 193 ± 4 | 130 ± 6 | 128 ± 6 | 141 ± 5 |
| MDP (3) + Cpd. 1 (1) | 192 ± 3 | 127 ± 4 | 114 ± 4 | 111 ± 3 |

Numerical values: average values ± standard error

TEST EXAMPLE 3

Antihypertensive Activity in Spontaneously Hypertensive Rats (SHR) by the Co-administration with a Diuretic Drug Compound 2: 2-ethoxy-1-[[2'-(2,5-dihydro-5-oxo-1,2,4-oxadiazole-3-yl)biphenyl-4-yl]methyl]-1H-benzimidazole-7-carboxylic acid HCT: hydrochlorothiazide Method: Male SHR of 20 week old were divided into 6 groups (five animals in one group). The respective groups were administered orally with the compound 2 (0.1 or 1 mg/kg,p.o.) or HCT (10 mg/kg, p.o.) alone or both drugs simultaneously once a day for two weeks. On the first, 7th and 14th day at 5 hr after the administration, blood pressure of each test animal was measured by the tail cuff method under unanesthesia.

Results: As shown in Table 3. Single dose of HCT (10 mg/kg/day, p.o.) did not show antihypertensive action. The compound 2 (0.1 and 1 mg/kg/day) showed dose dependent antihypertensive action. Efficiency of the antihypertensive activity of the compound 2 was enhanced by its co-administration with HCT. The antihypertensive activity observed by the combination of the compound 2 (0.1 mg/kg) and HCT was stronger or substantially the same as that observed by administering the compound 2 alone (1 mg/kg). This result shows that the co-use of both drugs can decrease the dosages of the respective drugs.

TABLE 3

Antihypertensive activity by the combination of compound 1 and the diuretic drug in spontaneously hypertensive rats

| Test group (dosage) mg/kg/day, p.o. | Before admin. | 1 day | 1 week | 2 weeks |
|---|---|---|---|---|
| | | (blood pressure: mmHg) | | |
| Control — | 205 ± 5 | 200 ± 5 | 202 ± 6 | 206 ± 5 |
| HCT (10) | 206 ± 5 | 188 ± 5 | 190 ± 5 | 195 ± 3 |
| Cpd. 2 (0.1) | 215 ± 5 | 187 ± 6 | 182 ± 6 | 191 ± 8 |
| Cpd. 2 (1) | 219 ± 7 | 175 ± 5 | 161 ± 4 | 165 ± 3 |
| HCT (10) + Cpd. 2 (0.1) | 222 ± 11 | 173 ± 5 | 168 ± 5 | 168 ± 3 |
| HCT (10) + Cpd. 2 (1) | 221 ± 6 | 170 ± 4 | 134 ± 3 | 142 ± 5 |

Numerical values: average values ± standard error (n = 7)

As is apparent from these test examples, the composition comprising the compound having angiotensin II antagonistic activity or a salt thereof and the compound having diuretic activity or the compound having calcium antagonistic activity enhances the action of the respective drug administered singly and can decrease the dosages of the respective drugs. As a result, suppression of the occurrence of undesirable side effects observed when these drugs are administered singly can be expected to a considerable extent.

Working Example

Formulation Examples

The pharmaceutical composition of angiotensin II-mediated diseases, formulated by combination of a compound having angiotensin II antagonistic activity represented by the formula (I) or a salt thereof and a compound having diuretic activity or a compound having calcium antagonistic activity, can be prepared by the prescriptions described as follows.

1. Capsules

| | | |
|---|---|---|
| (1) | 2-ethoxy-1-[[2'-(1H-tetrazol-5-yl)biphenyl-4-yl]methyl]-1H-benzimidazole-7-carboxylic acid | 1 mg |
| (2) | hydrochlorothiazide | 25 mg |
| (3) | lactose | 64 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatin capsule.

2. Tablets

| | | |
|---|---|---|
| (1) | 2-ethoxy-1-[[2'-(1H-tetrazol-5-yl)biphenyl-4-yl]methyl]-1H-benzimidazole-7-carboxylic acid | 1 mg |
| (2) | hydrochlorothiazide | 25 mg |
| (3) | lactose | 71.5 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

3. Injections

| | | |
|---|---|---|
| (1) | disodium 2-methylthio-1-[[2'-(1H-tetrazol-5-yl)biphenyl-4-yl]methyl]-1H-benzimidazole-7-carboxylate | 1 mg |
| (2) | furosemide | 20 mg |
| (3) | inositol | 89 mg |
| (4) | benzyl alcohol | 20 mg |
| | one ampoule | 130 mg |

(1), (2), (3) and (4) were dissolved in distilled water for injection to make the whole volume 2 ml, which was filled into an ampoule. The whole process was conducted under sterile conditions.

4. Capsules

| | | |
|---|---|---|
| (1) | (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 1 mg |
| (2) | hydrochlorothiazide | 25 mg |
| (3) | lactose | 64 mg |
| (4) | microcrystalline cellulose | 70 mg |
| (5) | magnesium stearate | 10 mg |
| | one capsule | 180 mg |

(1), (2),.(3), (4) and ½ of (5) were mixed and then granulated. To the granules was added the remainder of (5), and the whole formulation was filled into a gelatin capsule.

5. Tablets

| | | |
|---|---|---|
| (1) | (±)-1-(cyclohexyloxycarbonyloxy)ethyl 2-ethyoxy-1-[[2'-(1H-tetrazol-5-yl)biphenyl-4-yl]methyl]-1H-benzimidazole-7-carboxylate | 1 mg |
| (2) | hydrochlorothiazide | 25 mg |
| (3) | lactose | 71.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

6. Injections

| | | |
|---|---|---|
| (1) | disodium 2-ethoxy-1[[2'-(1H-tetrazol-5-yl)biphenyl-4-yl]methyl]-1H-benzimidazole-7-carboxylate | 1 mg |
| (2) | furosemide | 20 mg |
| (3) | inositol | 89 mg |
| (4) | benzyl alcohol | 20 mg |
| | one ampoule | 130 mg |

(1), (2), (3) and (4) were dissolved in distilled water for injection to make the whole volume 2 ml, which is filled into an ampoule. The whole process was conducted under sterile conditions.

7. Capsules

| | | |
|---|---|---|
| (1) | 2-butyl-1-[[2'-(1H-tetrazol-5-yl)biphenyl-4-yl]methyl]-1H-benzimidazole-7-carboxylic acid | 1 mg |
| (2) | hydrochlorothiazide | 25 mg |
| (3) | lactose | 64 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatin capsule.

| 8. Tablets | | |
|---|---|---|
| (1) | 2-butyl-1-[[2'-(1H-tetrazol-5-yl)biphenyl-4-yl]methyl]-1H-benzimidazole-7-carboxylic acid | 1 mg |
| (2) | hydrochlorothiazide | 25 mg |
| (3) | lactose | 71.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

| 9. Capsules | | |
|---|---|---|
| (1) | pivaloyloxymethyl 2-butyl-1-[[2'-(1H-tetrazol-5-yl)biphenyl-4-yl]methyl]-1H-benzimidazol-7-carboxylate | 1 mg |
| (2) | hydrochlorothiazide | 25 mg |
| (3) | lactose | 64 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole formulation was filled into a gelatin capsule.

| 10. Capsules | | |
|---|---|---|
| (1) | (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 2 mg |
| (2) | manidipine hydrochloride | 2 mg |
| (3) | lactose | 96 mg |
| (4) | microcrystalline cellulose | 70 mg |
| (5) | magnesium stearate | 10 mg |
| | one capsule | 180 mg |

(1), (2), (3), (4) and ½ of (5) were mixed and then granulated. To the granules was added the remainder of (5), and the whole was filled into a gelatine capsule.

| 11. Tablets | | |
|---|---|---|
| (1) | (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 2 mg |
| (2) | manidipine hydrochloride | 2 mg |
| (3) | lactose | 93.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

| 12. Tablets | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 1 mg |
| (2) | hydrochlorothiazide | 25 mg |
| (3) | lactose | 71.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granules were added the remainders of (6), (7) and (8), followed by subjecting the the mixture to compression molding.

| 13. Tablets | | |
|---|---|---|
| (1) | 2-ethoxy-1-[[2'-(2,5-dihydro-5-oxo-1,2,4-oxadiazol-3-yl)biphenyl-4-yl]methyl]-1H-benzimidazole-7-carboxylic acid | 2 mg |
| (2) | manidipine hydrochloride | 2 mg |
| (3) | lactose | 93.4 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 130 mg |

(1), (2), (3), (4), (5), ⅔ of (6), ⅔ of (7) and ½ of (8) were mixed and then granulated. To the granulates were added the remainders of (6), (7) and (8), followed by subjecting the mixture to compression molding.

| 14. Capsules | | |
|---|---|---|
| (1) | 2-ethoxy-1-[[2'-(1H-tetrazole-5-yl)biphenyl-4-yl]methyl]-1H-benzimidazole-7-carboxylic acid | 4~12 mg |
| (2) | hydrochlorothiazide | 6.25 mg |
| (3) | lactose | 64 mg |
| (4) | microcrystalline cellulose | 70 mg |
| (5) | magnesium stearate | 10 mg |
| | one capsule | 154.25~162.25 mg |

(1), (2), (3), (4) and ½ of (5) were mixed and then granulated. To the granules was added the remainder of (5), and the whole was filled into a gelatin capsule.

| 15. Tablets | | |
|---|---|---|
| (1) | 2-ethoxy-1-[[2'-(1H-tetrazol-5-yl)biphenyl-4-yl]methyl]-1H-benzimidazole-7-carboxylic acid | 4~12 mg |
| (2) | hydrochlorothiazide | 6.25 mg |
| (3) | lactose | 71.5 mg |
| (4) | corn starch | 20 mg |
| (5) | polyethylene glycol | 2.6 mg |
| (6) | hydroxypropyl cellulose | 4 mg |
| (7) | carmellose calcium | 5.6 mg |
| (8) | magnesium stearate | 0.4 mg |
| | one tablet | 114.35~122.35 mg |

(1), (2), (3), (4); (5), ⅔ of (6), ⅔ of (7) and ½ of (8) were mixed and then granulated. To the granules were added the remainders of (6), (7) and (8), followed by subjecting the mixture to compression molding.

| 16. Capsules | |
|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 4~12 mg |
| (2) hydrochlorothiazide | 6.25 mg |
| (3) lactose | 64 mg |
| (4) microcrystalline cellulose | 70 mg |
| (5) magnesium stearate | 10 mg |
| one capsule | 154.25~162.25 mg |

(1), (2), (3), (4) and ½ of (5) were mixed and then granulated. To the granules was added the remainder of (5), and the whole was filled into a gelatin capsule.

| 17. Tablets | |
|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 4~12 mg |
| (2) hydrochlorothiazide | 6.25 mg |
| (3) lactose | 71.4 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 114.35~122.35 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

| 18. Capsules | |
|---|---|
| (1) 2-ethoxy-1-[[2'-(1H-tetrazol-5-yl)biphenyl-4-yl]methyl]-1H-benzimidazole-7-carboxylic acid | 2 mg |
| (2) hydrochlorothiazide | 6.25~25 mg |
| (3) lactose | 64 mg |
| (4) microcrystalline cellulose | 70 mg |
| (5) magnesium stearate | 10 mg |
| one capsule | 152.25~171 mg |

(1), (2), (3), (4) and ½ of (5) were mixed and then granulated. To the granules was added the remainder of (5), and the whole was filled into a gelatin capsule.

| 19. Tablets | |
|---|---|
| (1) 2-ethoxy-1-[[2'-(1H-tetrazol-5-yl)biphenyl-4-yl]methyl]-1H-benzimidazole-7-carboxylic acid | 2 mg |
| (2) hydrochlorothiazide | 6.25~25 mg |
| (3) lactose | 71.5 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 112.35~131.1 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

| 20. Capsules | |
|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 2 mg |
| (2) hydrochlorothiazide | 6.25~25 mg |
| (3) lactose | 64 mg |
| (4) microcrystalline cellulose | 70 mg |
| (5) magnesium stearate | 10 mg |
| one capsule | 152.25~171 mg |

(1), (2), (3), (4) and ½ of (5) were mixed and then granulated. To the granules was added the remainder of (5), and the whole was filled into a gelatin capsule.

| 21. Tablets | |
|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 2 mg |
| (2) hydrochlorothiazide | 6.25~25 mg |
| (3) lactose | 71.4 mg |
| (4) corn starch | 20 mg |
| (5) polyethylene glycol | 2.6 mg |
| (6) hydroxypropyl cellulose | 4 mg |
| (7) carmellose calcium | 5.6 mg |
| (8) magnesium stearate | 0.4 mg |
| one tablet | 112.35~131.1 mg |

(1), (2), (3), (4), (5), ⅔ of (6), ⅔ of (7) and ½ of (8) were mixed and then granulated. To the granules were added the remainders of (6), (7) and (8), followed by subjecting the mixture to compression molding.

What is claimed is:

1. A pharmaceutical composition, which comprises at least one of (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate, 2-ethoxy-1-[[2'-(1H-tetrazol-5-yl)biphenyl-4-yl]methyl]-1H-benzimidazole-7-carboxylic acid, or 2-ethoxy-1-[[2'-(2,5-dihydro-5-oxo-1,2,4-oxadiazol-3-yl)biphenyl-4-yl]methyl]-1H-benzimidazole-7-carboxylic acid or a pharmaceutically acceptable salt thereof in combination with trichloromethiazide or indapamide.

2. A method for the prophylaxis or treatment of angiotensin II-mediated disease in a mammal in need thereof which comprises administering an effective amount of at least one of (±)-1-cyclohexyloxycarbonyloxy)ethyl 2-ethoxy-1-[[2'-(1H-tetrazol-5-yl)biphenyl-4-yl]methyl]-1H-benzimidazole-7-carboxylate, 2-ethoxy-1-[[2'-(1H-tetrazol-5-yl)biphenyl-4-yl]methyl]-1H-benzimidazole-7-carboxylic acid, or 2-ethoxy-1-[[2'-(2,5-dihydro-5-oxo-1,2,4,-oxadiazol-3-yl)biphenyl-4-yl]methyl]]-1H-benzimidazole-7-carboxylic acid, or a pharmaceutically acceptable salt thereof, in combination with an effective amount of trichloromethiazide or indapamide.

3. A method according to claim 2, wherein the disease is hypertension, cardiac insufficiency, ischemic peripheral circulation disorders, myocardial ischemia, vein insufficiency, progressive cardiac unsufficiency after myocardial infarction, diabetic nephritides, nepbritis, arteriosclerosis, hyperaldosteronism, dermatosclerosis, glomerulosclerosis, renal insufficiency, central nervous system diseases, sensory disorders, Alzheimer's disease, deficiency or memory, depression, amnesia, senile dementia, anxiety neurosis, catatonia or indisposition, glaucoma, or intraocular high pressure.

4. A method according to claim 2, wherein the disease is hypertension.

* * * * *